United States Patent [19]
Platt, Jr. et al.

[11] Patent Number: 5,669,907
[45] Date of Patent: Sep. 23, 1997

[54] PLASMA ENHANCED BIPOLAR ELECTROSURGICAL SYSTEM

[75] Inventors: Robert C. Platt, Jr.; Dale F. Schmaltz, both of Boulder; Steve Buysee, Longmont, all of Colo.

[73] Assignee: Valleylab Inc., Boulder, Colo.

[21] Appl. No.: 386,898

[22] Filed: Feb. 10, 1995

[51] Int. Cl.$^6$ ................................................ A61B 17/36
[52] U.S. Cl. .................. 606/48; 606/34; 606/39; 606/41
[58] Field of Search ............ 606/27, 28, 32–41, 606/45–50

[56] References Cited

U.S. PATENT DOCUMENTS

| | | |
|---|---|---|
| Re. 34,432 | 11/1993 | Bertrand . |
| 3,838,242 | 9/1974 | Goucher ................... 606/40 |
| 3,903,891 | 9/1975 | Brayshaw ................... 606/27 |
| 3,970,088 | 7/1976 | Morrison . |
| 3,987,795 | 10/1976 | Morrison . |
| 4,040,426 | 8/1977 | Morrison et al. . |
| 4,041,952 | 8/1977 | Morrison, Jr. et al. . |
| 4,043,342 | 8/1977 | Morrison, Jr. . |
| 4,060,088 | 11/1977 | Morrison, Jr. et al. . |
| 4,492,231 | 1/1985 | Auth . |
| 4,781,175 | 11/1988 | McGreevy et al. . |
| 4,890,610 | 1/1990 | Kirwan, Sr. et al. . |
| 4,901,719 | 2/1990 | Trenconsky et al. . |
| 4,901,720 | 2/1990 | Bertrand . |
| 5,217,457 | 6/1993 | Delahuerya et al. ................... 606/45 |

*Primary Examiner*—David M. Shay
*Attorney, Agent, or Firm*—Peter C. Richardson; Lawrence C. Akers; Aaron Passman

[57] ABSTRACT

A surgical system has a multiple electrode electrosurgical capability in combination with a gas plasma capability for delivery of electrosurgical energy to the tissue or bodily fluids of a patient. The system includes a holder, a source of electrical energy, electrodes connected to the source of electrical energy, one or more passages carried on the holder for transporting ionizable gas, and a source of ionizable gas of a selectable flow rate. The gas passages may include at least one electrode extending toward the operative site. The gas passages may include a part that creates a vortex in the gas flow. The electrodes may be coaxially placed in the gas passages. The system may also be configured such that two electrodes are each shrouded by the ionized gas so that the electrosurgical energy is conducted to the tissue or bodily fluids of the operative site by passing along conductive pathways in the ionized gas from each electrode. There may also be a dielectric barrier between the conductive pathways. The system may also be configured such that one of the multiple electrodes is substantially in contact with the tissue or bodily fluids of the operative site and another of the multiple electrodes is in the circuit through the conductive pathway of the ionized gas flow so that electrosurgical energy is conducted through the tissue or bodily fluids of the operative site and between the electrodes. Methods of manufacture and use for the system are also claimed.

7 Claims, 4 Drawing Sheets

PLASMA ENHANCED BIPOLAR ELECTROSURGICAL SYSTEM

FIELD OF THE INVENTION

This relates to a surgical system which has an electrosurgical capability in combination with a gas plasma capability for delivery of electrosurgical energy to the tissue or bodily fluids of a patient, and more particularly to the surgical system wherein the electrosurgical capability is other than monopolar.

BACKGROUND OF THE DISCLOSURE

The use of high frequency electrical energy is well known in the field of surgery. Many surgical procedures make use of high frequency electrical energy, which is also known as electrosurgical energy. Tissue of a patient may be cut using electrosurgical energy, and bodily fluids may also be coagulated using electrosurgical energy. The means of applying the electrosurgical energy to the patient is important so that desirable surgical effects can be achieved and undesirable effects can be minimized or avoided.

Electrosurgical instruments may be divided into several categories based on their means for applying the electrosurgical energy. One category may be referred to as "monopolar" devices. Monopolar electrosurgical devices have only one active electrode located on the electrosurgical instrument, and require that a separate return electrode be attached to the patient at a location away from the surgical site. In monopolar electrosurgery, the electrosurgical energy flows through the active electrode on the instrument, and then flows through the patient's body to the return electrode. Monopolar devices have been found to be effective in surgical procedures where cutting and coagulation of tissue are required, and where stray electrical currents will not pose a substantial risk to the patient.

Another category of electrosurgical devices may be referred to as "bipolar" devices. Bipolar electrosurgical devices have both an active electrode and a return electrode located on the surgical instrument. In a bipolar electrosurgical device, electrosurgical energy flows through the active electrode on the surgical instrument to the tissue of a patient, then flows a short distance through the tissue to the return electrode which is also on the surgical instrument. The electrosurgical effects are substantially localized to a small area of tissue which is disposed between the two electrodes on the surgical instrument. Bipolar electrosurgical devices have been found to be useful for certain surgical procedures where stray electrical currents may pose a hazard to the patient, or where other procedural concerns require close proximity of the active and return electrodes. Surgical operations involving bipolar electrosurgery often require methods and procedures which differ substantially from the methods and procedures involving monopolar electrosurgery.

There are also variations of bipolar devices which are known in the field of electrosurgery. For example, a "sesquipolar" device is essentially a bipolar device in which one electrode has an effective contact area on the tissue which is substantially larger than the contact area of the other electrode.

Monopolar electrosurgical energy has been used in combination with argon gas which has been ionized to form a plasma. The plasma forms a conductive path to transmit electrosurgical energy. Therefore, the plasma may conduct electrosurgical energy to the patient without the need for physical contact between the patient and an electrode. Transmission of electrosurgical energy through a gas plasma is more desirable than mere arcing of the electrosurgical energy because of the degree of control that is available to the surgeon when the electrosurgical energy is directed through the plasma. Argon gas is used to create a plasma in monopolar electrosurgical systems. Other ionized gases besides argon are known but not commonly used for surgery. No bipolar electrosurgical device has heretofore been used in combination with a plasma.

U.S. Pat. No. 4,060,088 relates to an electrosurgical method and apparatus for coagulation by fulguration. The apparatus has source of inert ionized gas which surrounds a tubular electrosurgical electrode. There is also disclosed a source of periodic bursts of electrosurgical energy used to initiate the plasma arc. Only one electrode is disclosed on the electrosurgical apparatus so that the device is monopolar.

U.S. Pat. No. 4,781,175 has an ionizable gas jet to the tissue to clear bodily fluids and coagulate or achieve fulguration in the form of an improved eschar. The instrument is a conduit for the flow of gas at a predetermined flow rate about a centrally located electrode for electrosurgical energy. Circuitry and computer logic are shown to control the gas jet flow and the electrosurgical energy. No return path for the electrosurgical energy is provided.

U.S. Pat. No. 4,901,720 and the reissue thereof U.S. Pat. No. Re. 34,432 deal with the rate of burst energy pulses, applied to maintain leakage current within acceptable limits while having sufficient ionization during initiation and use. Circuit and logic diagrams are provided to control the burst energy by pulse width, resonance, waveform and output.

U.S. Pat. Nos. 3,970,088, 3,987,795 and 4,043,342 have sesquipolar electrodes on an instrument used to apply electrosurgical energy to an operative site. The electrodes are of different size wherein the return electrode is larger being in the range of about 2 to 200 times the surface area of the other active electrode. In the '342 patent the return electrode is biased by a spring to extend outwardly relative to the active electrode. No ionizable gas is disclosed in connection with sesquipolar electrodes.

U.S. Pat. No. 4,041,952 has a switch on a forceps that can be used as monopolar or bipolar as needed by the surgeon during treatment of the patient with electrosurgery. U.S. Pat. No. 4,890,610 has a pair of bipolar forceps composed of coined metallic conductive blades that are each overmolded with a plastic insulator to leave exposed tips at the patient end and connector terminals for electrosurgical energy at the opposite ends. U.S. Pat. No. 4,492,231 has a bipolar circuit to provide non stick coagulation therebetween by use of a good thermal conductor and minimal contact relative to the volume of conductive material in the tines of the forceps. Not one thing in any of these bipolar forcep teachings has ionized gas to direct and transmit the electrosurgical energy.

U.S. Pat. No. 4,060,088 also has a monopolar electrosurgical unit in combination with an ionizable gas delivery system. U.S. Pat. No. 4,040,426 has an improved method and apparatus for initiating an electrical discharge in the ionizable gas. U.S. Pat. No. 4,901,719 has a monopolar electrosurgical unit in combination with an ionizable gas delivery system, where there is also an improvement relating to the gas conducting means.

The disclosures of the aforesaid references are incorporated by reference and made a part hereof.

SUMMARY OF THE INVENTION

It is a general object of this invention to combine a bipolar electrosurgical capability with a gas plasma capability. This combination has heretofore not been appreciated by artisans in the medical device industry. Several embodiments of this system are described which provide for alternative delivery schemes for the electrosurgical energy. Methods of using this system are also described.

A surgical system is described for use by a surgeon on the tissue or bodily fluids at an operative site of a patient. The surgical system has multiple electrodes, wherein the electrodes are contained within a surgical instrument. The surgical system also has a gas plasma capability. Electrical energy is transmitted between the electrodes at the surgical site and through the tissue or bodily fluids of a patient.

The surgical system comprises the following elements: A holder for the surgeon to use during application to a patient of electrosurgical effects; a distal end on the holder near the patient; a proximal end on the holder near the surgeon; a source of electrical energy for producing electrosurgical effects on the tissue or bodily fluids of the patient, the source of electrical energy having an alternating potential thereacross so that energy flows in the circuit connected thereto, the source including terminals of substantially different potential; electrodes extending from the distal end of the holder toward the operative site, the electrodes connected to the source of electrical energy, wherein each of the terminals is connected to at least one of the electrodes; one or more passages carried on the holder for transporting ionizable gas toward the vicinity of the operative site, and a source of ionizable gas of a selectable flow rate connected to the proximal end of the holder and in fluid communication with the one or more passages for the transport of ionizable gas therethrough.

In one embodiment, each passage in the surgical system has at least one electrode extending distally therefrom toward the operative site for directing the selectable flow of ionized gas along each electrode toward the tissue or bodily fluid of the patient. The electrosurgical energy is conducted to the tissue or bodily fluids of the operative site by passing along conductive pathways in the ionized gas around each electrode. There may be a barrier between the conductive pathways, the barrier may be a dielectric of solid or gaseous form insuring the flow of electrical energy along the conductive pathways of ionized gas and through the tissue or bodily fluids.

In another embodiment, one of the multiple electrodes may be substantially in contact with the tissue or bodily fluids of the operative site and another of the multiple electrodes may be in the circuit through the conductive pathway of the ionized gas flow so that electrosurgical energy is conducted through the tissue or bodily fluids of the operative site and between the electrodes. The electrode in substantial contact with the tissue or bodily fluid may be sized to minimize current density so as to diffuse electrosurgical effects thereat. The electrode in contact may be shaped to smoothly engage the tissue or bodily fluids over a larger area than the non contact electrode or electrodes would if in contact. Alternatively, the electrode in substantial contact with the tissue or bodily fluid may be sized to increase current density collected thereby sufficiently so as to cut or part the tissue or bodily fluids thereat by electrosurgical effects. This may be accomplished by having the electrode in contact shaped to engage with an end thereof the tissue or bodily fluids over a small area. The electrode in contact may include the passage with ionizable gas to shroud the operative site whereat the tissue or bodily fluids are cut or parted. The contact electrode or electrodes may also be coated with a dielectric material to prevent direct flow of electrical energy between the conductive pathway of ionized gas and the contact electrode or electrodes and to insure that the flow is through the tissue or bodily fluids of the operative site.

The surgical system may have a part in the passage which creates a vortex in the flow therethrough, imparting a density gradient across the flow with greater density away from an axis along the direction of the passage. The source of ionizable gas may have a piece therein that creates a vortex in the flow through the passage imparting a density gradient across the flow with greater density away from an axis along the direction of the passage.

The surgical system may have the electrodes coaxially centered within the passages. Also, the electrodes may be positionable relative to each other to extend toward the tissue or bodily fluid and from the holder.

In another embodiment, each passage may be electrically conductive and is electrically connected between a terminal of the source of electrical energy and the electrode associated therewith.

A method of using a surgical system is claimed where the method including the steps of: Having a holder for the surgeon to use during application to a patient of electrosurgical effects in the multiple electrode circuit with a distal end on the holder near the patient and a proximal end on the holder near the surgeon; generating high frequency alternating electrical potential energy for producing electrosurgical effects on the tissue or bodily fluids of the patient, where the electrical potential is generated by a source of electrical energy having terminals of substantially different potential; connecting electrodes to the source of electrical energy such that each of the terminals is connected to at least one of the electrodes; extending the electrodes from the distal end of the holder toward the operative site; carrying one or more passages on the holder for transporting ionizable gas toward the vicinity of the operative site, and selecting a flow rate from a source of ionizable gas which is connected to the proximal end of the holder and in fluid communication with the one or more passages for the transport of ionizable gas therethrough. The method of using the surgical system may also have an additional step of imparting a density gradient across the flow of the ionized gas in the passages whereby the density gradient is greater away from an axis along the direction of the passage.

The method of using the surgical system may also include an additional step of extending at least one electrode from each passage, where the electrode is extended distally therefrom toward the operative site for directing the selectable flow of ionized gas along each electrode toward the tissue or bodily fluid of the patient. The method of using the surgical system may also include the step of erecting a barrier between the conductive pathways, where the barrier is a dielectric of solid or gaseous form insuring the flow of electrical energy along the conductive pathways of ionized gas and through the tissue or bodily fluids.

Another method of using the surgical system includes the step of contacting one of the multiple electrodes substantially with the tissue or bodily fluids of the operative site and connecting another of the multiple electrodes in the circuit through the conductive pathway of the ionized gas flow so that electrosurgical energy is conducted through the tissue or bodily fluids of the operative site and between the electrodes. The method may have an additional step of coating the contact electrode with a dielectric material to prevent direct flow of electrical energy between the conductive pathway of ionized gas and the contact electrode or electrodes and to insure that the flow is through the tissue or bodily fluids of the operative site. The method may also have the additional step of cutting the tissue with the electrode which is in substantial contact with the tissue and is sized to increase current density collected thereby sufficiently so as to cut or part the tissue thereat by electrosurgical effects. Alternatively, the method may have the step of coagulating the tissue or bodily fluid with the electrode which is in substantial contact with the tissue or bodily fluid and is sized to minimize current density so as to diffuse electrosurgical effects thereat. The method may also have an additional step of coagulating or desiccating the tissue or bodily fluid which is located primarily where the ionized gas contacts the tissue or bodily fluids.

Yet another method of using the surgical system has a step of shrouding each of two electrodes with the ionized gas so that the electrosurgical energy is conducted to the tissue or bodily fluids of the operative site by passing along conductive pathways in the ionized gas from each electrode.

A method of manufacture for the surgical system includes the steps of making at least a portion of at least one of the passages from an electrically conductive material, and electrically connecting at least one electrically conductive portion of the passage between the source of electrical energy and one of the electrodes which is also located on the holder.

DETAILED DESCRIPTION OF THE INVENTION

Figure 1:
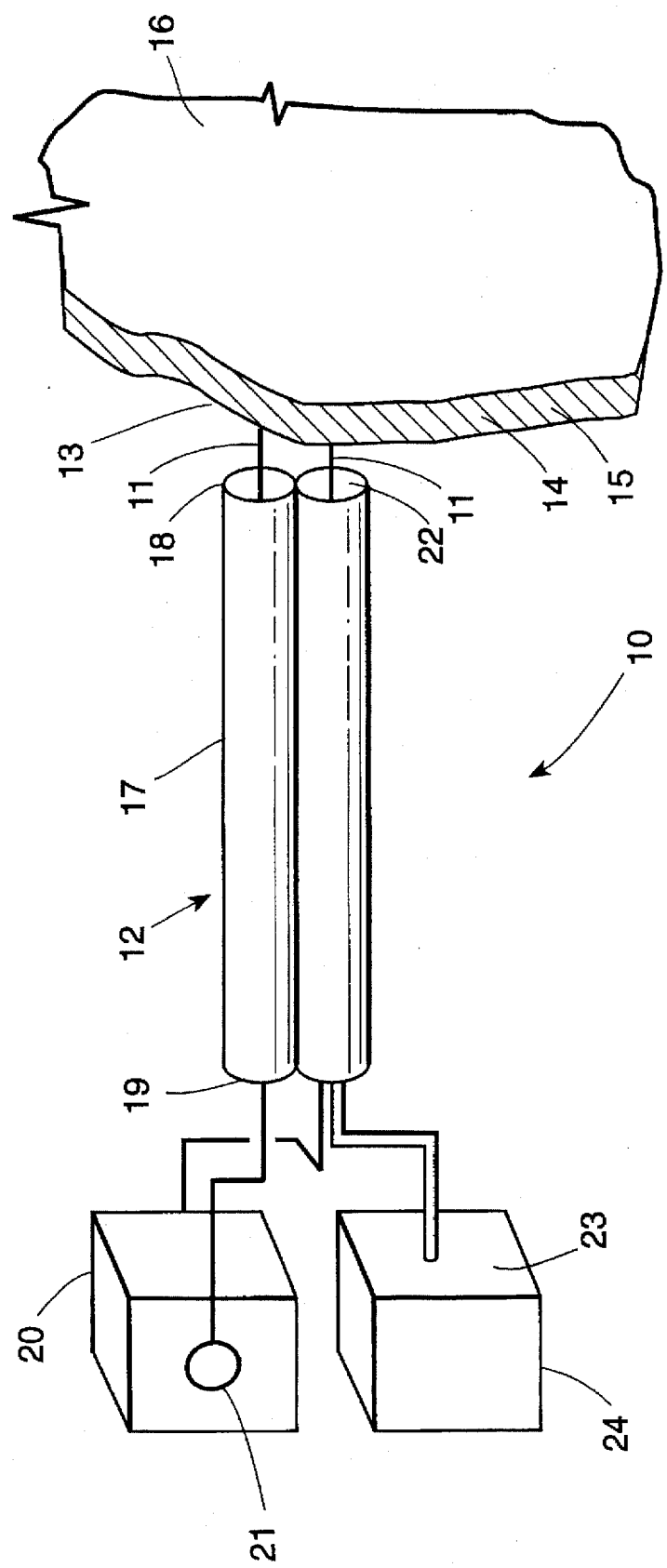
FIG. 1 is a schematic drawing of a Plasma Enhanced Bipolar Electrosurgical System.

A surgical system 10 is shown in FIG. 1 for use by a surgeon on the tissue 14 or bodily fluids 15 at a surgical site 13 of a patient 16. The surgical system 10 has multiple electrodes 11, wherein the electrodes 11 are contained within a surgical instrument 12. The surgical system 10 also has a gas plasma capability. Electrical energy is transmitted between the electrodes 11 at the surgical site 13 and through the tissue 14 or bodily fluids 15 of a patient 16.

The surgical system 10 comprises the following elements: A holder 17 for the surgeon to use during application to a patient 16 of electrosurgical effects; a distal end 18 on the holder 17 near the patient 16; a proximal end 19 on the holder 17 near the surgeon; a source of electrical energy 20 for producing electrosurgical effects on the tissue 14 or bodily fluids 15 of the patient 16, the source of electrical energy 20 having an alternating potential thereacross so that energy flows in the circuit connected thereto, the source 20 including terminals 21 of substantially different potential; electrodes 11 extending from the distal end 18 of the holder 17 toward the operative site 13, the electrodes 11 connected to the source of electrical energy 20, wherein each of the terminals 21 is connected to at least one of the electrodes 11; one or more passages 22 carried on the holder 17 for transporting ionizable gas 23 toward the vicinity of the operative site 13, and a source of ionizable gas 24 of a selectable flow rate connected to the proximal end 19 of the holder 17 and in fluid communication with the one or more passages 22 for the transport of ionizable gas 23 therethrough.

Figure 4:
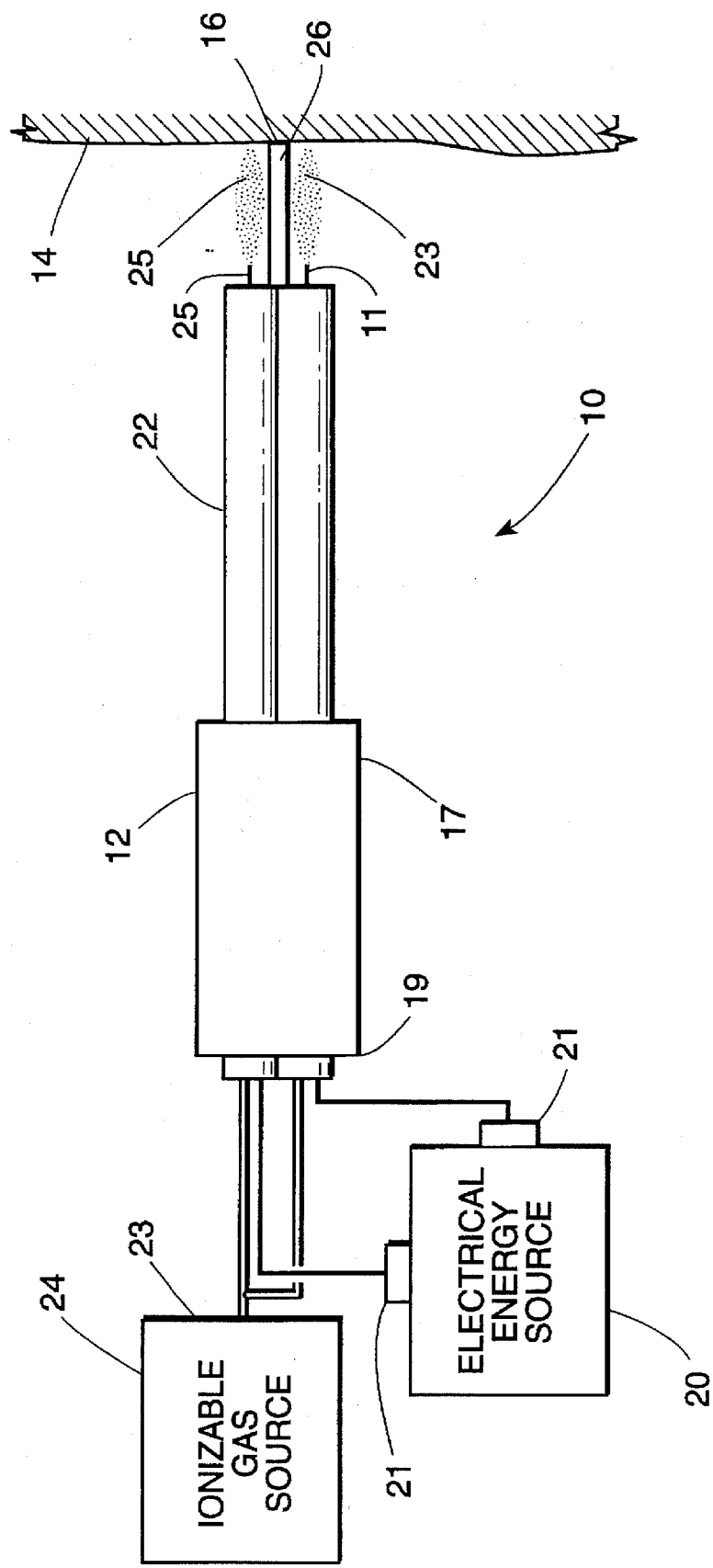
FIG. 4 is a schematic block diagram of a third embodiment of a Plasma Enhanced Bipolar Electrosurgical System.

In one embodiment, each passage 22 in the surgical system 10 has at least one electrode 11 extending distally therefrom toward the operative site 13 for directing the selectable flow along each electrode 11 toward the tissue 14 or bodily fluid 15 of the patient 16. Alternatively, as shown in FIG. 4, two electrodes 11 may be each shrouded by the ionized gas 23 so that the electrosurgical energy is conducted to the tissue 14 or bodily fluids 15 of the operative site 16 by passing along conductive pathways 25 in the ionized gas 23 from each electrode 11. There may be a barrier 26 between the conductive pathways 25, the barrier 26 may be a dielectric of solid or gaseous form insuring the flow of electrical energy along the conductive pathways 25 of ionized gas 23 and through the tissue 14 or bodily fluids 15.

Figure 2:
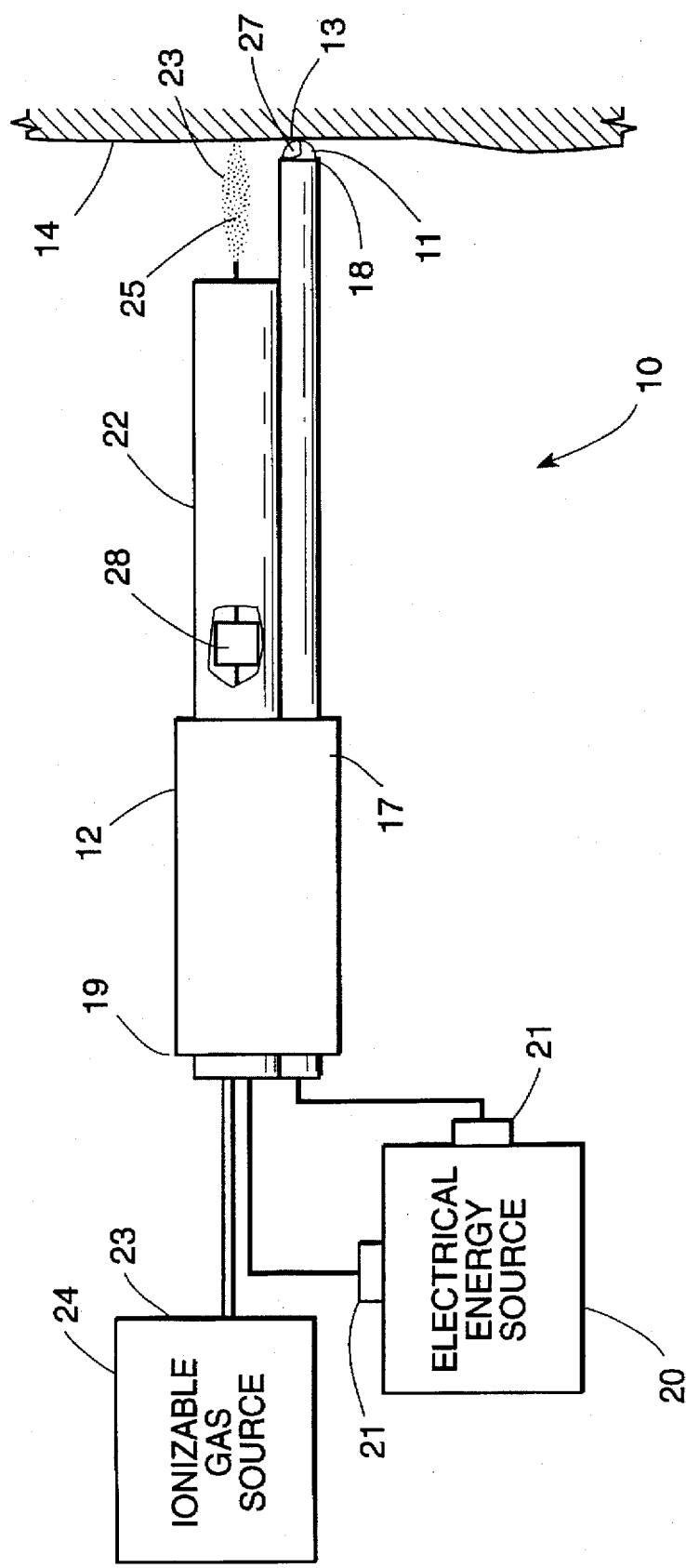
FIG. 2 is a schematic block diagram of a first embodiment of a Plasma Enhanced Bipolar Electrosurgical System with a partial section to disclose a part in the passage.
Figure 3:
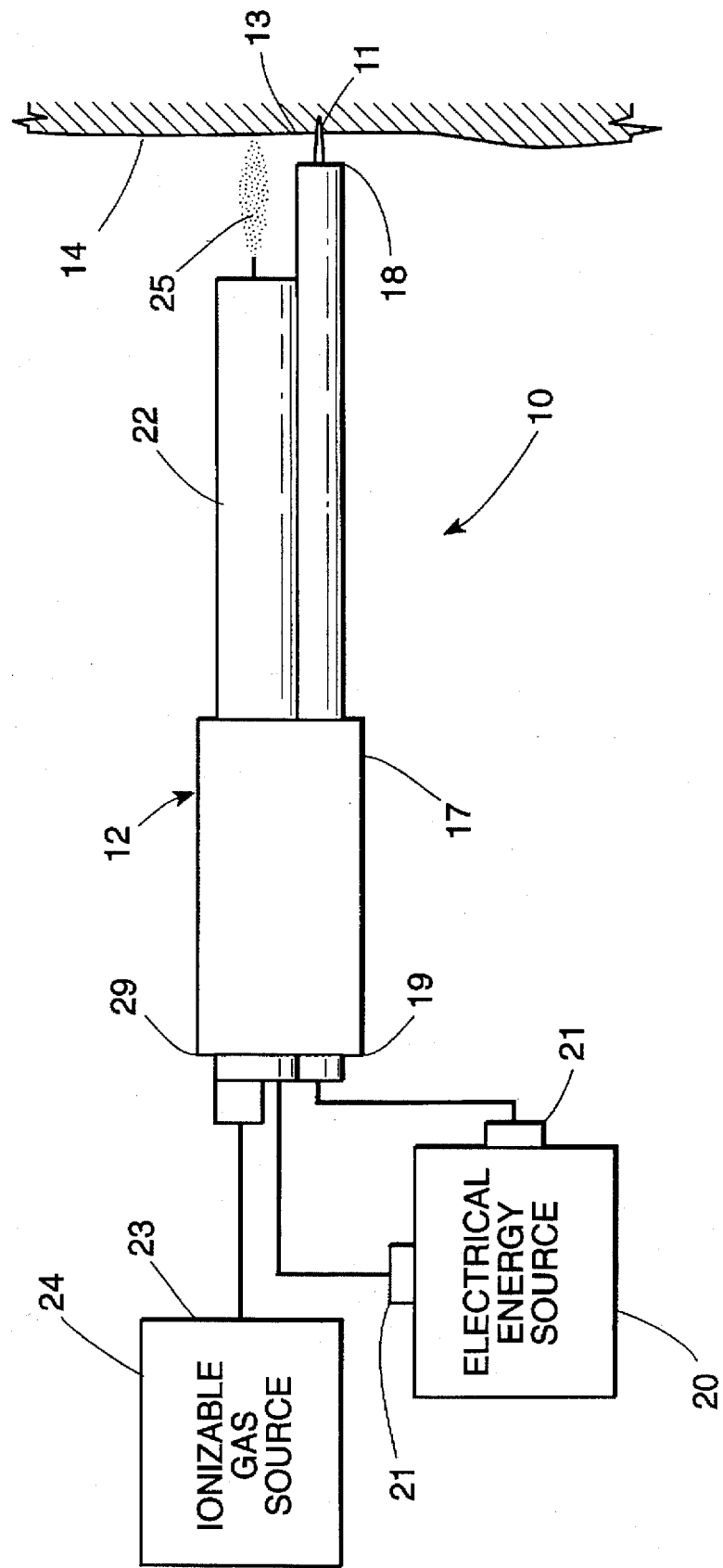
FIG. 3 is a schematic block diagram of a second embodiment of a Plasma Enhanced Bipolar Electrosurgical System.

In another embodiment, shown in FIG. 2, one of the multiple electrodes 11 may be substantially in contact with the tissue 14 or bodily fluids 15 of the operative site 16 and another of the multiple electrodes 11 may be in the circuit through the conductive pathway 25 of the ionized gas flow 23 so that electrosurgical energy is conducted through the tissue 14 or bodily fluids 15 of the operative site 16 and between the electrodes 11. The electrode 11 in substantial contact with the tissue 14 or bodily fluid 15 may be sized to minimize current density so as to diffuse electrosurgical effects thereat. The electrode 11 in contact may be shaped to smoothly engage the tissue 14 or bodily fluids 15 over a larger area than the non contact electrode 11 or electrodes 11 would if in contact, as shown in FIG. 2. Alternatively, as shown in FIG. 3, the electrode 11 in substantial contact with the tissue 14 or bodily fluid 15 may be sized to increase current density collected thereby sufficiently so as to cut or part the tissue 14 or bodily fluids 15 thereat by electrosurgical effects. This may be accomplished by having the electrode 11 in contact shaped to engage with an end thereof the tissue 14 or bodily fluids 15 over a small area. The electrode 11 in contact may include the passage 22 with ionizable gas 23 to shroud the operative site 13 whereat the tissue 14 or bodily fluids 15 are cut or parted. As shown in FIG. 2, the contact electrode 11 or electrodes 11 may also be coated with a dielectric material 27 to prevent direct flow of electrical energy between the conductive pathway 25 of ionized gas 23 and the contact electrode 11 or electrodes 11 and to insure that the flow is through the tissue 14 or bodily fluids 15 of the operative site 13.

The surgical system 10 may have a part 28 in the passage 22 which creates a vortex in the flow therethrough, imparting a density gradient across the flow with greater density away from an axis along the direction of the passage 22, as shown in FIG. 2. The source of ionizable gas 24 may have a piece 29 therein that creates a vortex in the flow therethrough imparting a density gradient across the flow with greater density away from an axis along the direction of the passage 22, as shown in FIG. 3.

The surgical system may have the electrodes 11 coaxially centered within the passages 22. Also, the electrodes 11 may be positionable relative to each other to extend toward the tissue 14 or bodily fluid 15 and from the holder 17.

A method of using a surgical system 10 is claimed where the method including the steps of: Having a holder 17 for the surgeon to use during application to a patient 16 of electrosurgical effects in the multiple electrode 11 circuit with a distal end 18 on the holder 17 near the patient 16 and a proximal end 19 on the holder 17 near the surgeon; generating high frequency alternating electrical potential energy for producing electrosurgical effects on the tissue 14 or bodily fluids 15 of the patient 16, where the electrical potential is generated by a source of electrical energy 20 having terminals 21 of substantially different potential; connecting electrodes 11 to the source of electrical 20 such that each of the terminals 21 is connected to at least one of the electrodes 11; extending the electrodes 11 from the distal end 18 of the holder 17 toward the operative site 13; carrying one or more passages 22 on the holder 17 for transporting ionizable gas 23 toward the vicinity of the operative site 13, and selecting a flow rate from a source of ionizable gas 24 which is connected to the proximal end 19 of the holder 17 and in fluid communication with the one or more passages 22 for the transport of ionizable gas 23 therethrough. The method of using the surgical system 10 may also have an additional step of imparting a density gradient across the flow of the ionized gas 23 in the passages 22 whereby the density gradient is greater away from an axis along the direction of the passage 22.

The method of using the surgical system 10 may also include the an additional step of extending at least one electrode 11 from each passage 22, where the electrode 11 is extended distally therefrom toward the operative site 13 for directing the selectable flow along each electrode 11 toward the tissue 14 or bodily fluid 15 of the patient 16. The method of using the surgical system 10 may also include the step of erecting a barrier 26 between the conductive pathways, where the barrier 26 is a dielectric of solid or gaseous form insuring the flow of electrical energy along the conductive pathways 25 of ionized gas 23 and through the tissue 14 or bodily fluids 15.

Another method of using the surgical system 10 includes the step of contacting one of the multiple electrodes 11 substantially with the tissue 14 or bodily fluids 15 of the operative site 13 and connecting another of the multiple electrodes 11 in the circuit through the conductive pathway 25 of the ionized gas 23 flow so that electrosurgical energy is conducted through the tissue 14 or bodily fluids 15 of the operative site 13 and between the electrodes 11. The method may have an additional step of coating the contact electrode 11 with a dielectric material 27 to prevent direct flow of electrical energy between the conductive pathway 25 of ionized gas 23 and the contact electrode 11 or electrodes 11 and to insure that the flow is through the tissue 14 or bodily fluids 15 of the operative site 16. The method of may also have the additional step of cutting the tissue 14 with the electrode 11 which is in substantial contact with the tissue 11 and is sized to increase current density collected thereby sufficiently so as to cut or part the tissue 14 thereat by electrosurgical effects. Alternatively, the method may have the step of coagulating the tissue 14 or bodily fluid 15 with the electrode 11 which is in substantial contact with the tissue 14 or bodily fluid 15 and is sized to minimize current density so as to diffuse electrosurgical effects thereat.

Yet another method of using the surgical system 10 has a step of shrouding each of two electrodes 11 with the ionized gas 23 so that the electrosurgical energy is conducted to the tissue 14 or bodily fluids 15 of the operative site 13 by passing along conductive pathways 25 in the ionized gas 23 from each electrode 11.

A method of manufacture for the surgical system 10 includes the steps of making at least a portion of at least one of the passages 22 from an electrically conductive material, and electrically connecting at least one electrically conductive portion of the passage 22 between the source of electrical energy 20 and one of the electrodes 11 which is also located on the holder 17.

What is claimed is:

1. A surgical system comprising:

a holder having a hollow interior which forms at least one passage;

a distal end on the holder;

a proximal end on the holder;

a source of electrosurgical energy having first and second terminals with an alternating potential thereacross;

first and second electrodes attached to the holder, wherein the first and second terminals are electrically connected to the first and second electrodes, respectively;

a source of ionizable gas of a selectable flow rate connected to the proximal end of the holder and in fluid communication with the at least one passage for transport of ionizable gas therethrough, and an electrical circuit including the source of electrosurgical energy, and the first and second electrodes, whereby electrosurgical energy creates ionized conductive pathways in the ionizable gas, the ionized conductive pathways forming at least a portion of the electrical circuit between the first and second electrodes.

2. The surgical system of claim 1 wherein the at least one passage has at least one electrode extending distally therethrough.

3. The surgical system of claim 1 wherein the first and second electrodes are each shrouded by the ionizable gas so that the electrosurgical energy is conducted through the conductive pathways.

4. The surgical system of claim 1 wherein the passage is a tube and the electrode is coaxially centered therein.

5. The surgical system of claim 1 wherein the second electrode is in electrical contact with the ionizable gas flow so that electrosurgical energy is conducted between the first and second electrodes.

6. The surgical system of claim 5 wherein the first electrode is sized to minimize current density so as to diffuse electrosurgical effects thereat.

7. The surgical system of claim 5 wherein the first electrode is coated with a dielectric material.

* * * * *